United States Patent [19]

Zentner et al.

[11] Patent Number: 4,994,273
[45] Date of Patent: Feb. 19, 1991

[54] SOLUBILITY MODULATED DRUG DELIVERY DEVICE

[75] Inventors: Gaylen M. Zentner, Lawrence; Gregory A. McClelland, Lenexa, both of Kans.

[73] Assignee: Merck & Co., Inc., Rahway, N.J.

[21] Appl. No.: 384,116

[22] Filed: Jul. 20, 1989

Related U.S. Application Data

[63] Continuation-in-part of Ser. No. 115,487, Nov. 2, 1987, abandoned.

[51] Int. Cl.$^5$ .............................. A61F 13/00
[52] U.S. Cl. .................... 424/422; 424/427; 424/435; 424/437; 424/449; 424/473
[58] Field of Search ............ 424/422, 427, 435, 437, 424/449, 473,

[56] References Cited

U.S. PATENT DOCUMENTS

| | | | |
|---|---|---|---|
| 2,846,057 | 2/1954 | Polin | 206/5 |
| 2,928,770 | 7/1958 | Bardani | 167/82 |
| 3,538,214 | 11/1970 | Polli | 424/19 |
| 3,845,770 | 11/1974 | Theeuwes et al. | 424/427 |
| 3,957,523 | 5/1976 | Ohno et al. | 106/189 |
| 3,993,072 | 11/1976 | Zaffaroni | 128/260 |
| 4,160,452 | 7/1979 | Theeuwes | 128/260 |
| 4,200,098 | 4/1980 | Ayer et al. | 424/422 |
| 4,217,898 | 8/1980 | Theeuwes | 128/260 |
| 4,235,236 | 11/1980 | Theeuwes | 128/260 |
| 4,244,941 | 1/1981 | Lerk | 424/21 |
| 4,256,108 | 3/1981 | Theeuwes | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,326,525 | 4/1982 | Swanson | 424/433 |
| 4,557,925 | 12/1985 | Lindahl et al. | 424/19 |
| 4,755,180 | 7/1988 | Ayer et al. | 424/469 |

OTHER PUBLICATIONS

J. Pharm. Sci. 72, pp. 772–775.

Primary Examiner—Thurman K. Page
Assistant Examiner—P. L. Prater
Attorney, Agent, or Firm—Melvin Winokur; Joseph F. DiPrima

[57] ABSTRACT

A solubility modulated drug delivery device for controlled release of a therapeutically active ingredient into an environment of use is disclosed. The device comprises a core composition of a solubility modulating agent consisting of a complexing agent or a surfactant and a diffusible, water soluble, therapeutically active agent. The core composition is surrounded by a water insoluble semipermeable wall which is substantially impermeable to the core composition and permeable to the fluids in the environment of use and contains apertures through which active agent is released.

18 Claims, 3 Drawing Sheets

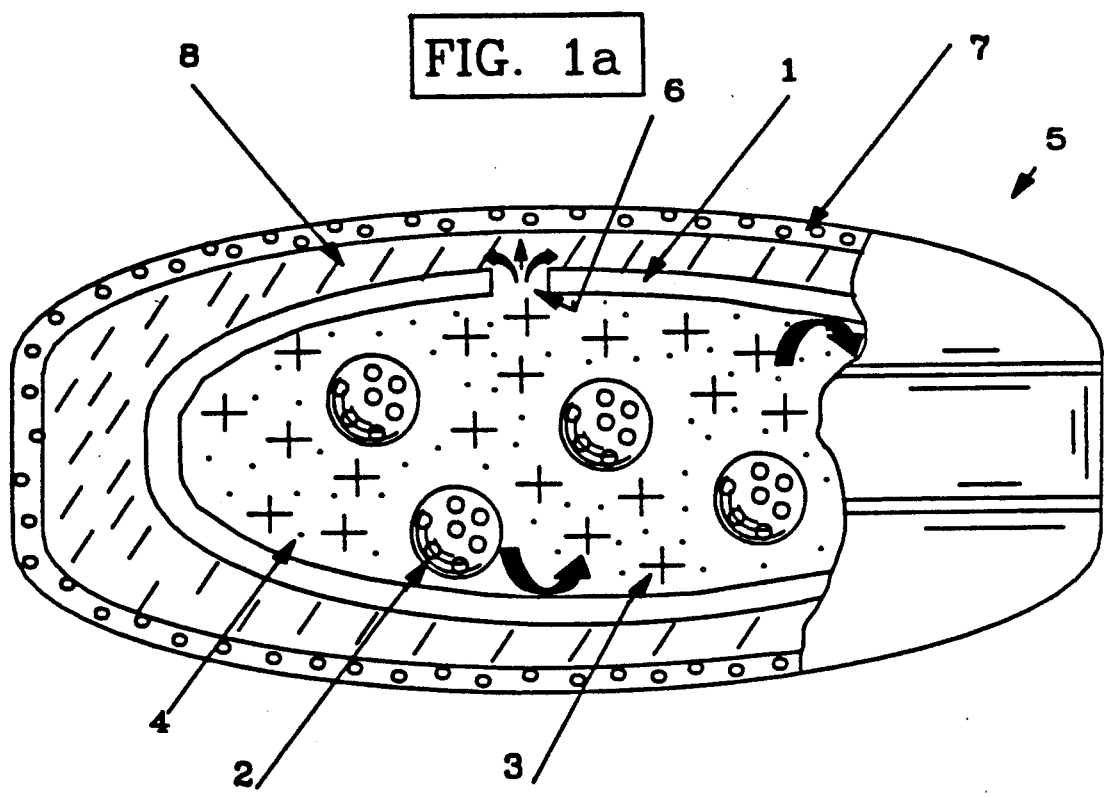

SOLUBILITY MODULATED DRUG DELIVERY DEVICE

This is a continuation-in-part of copending application Ser. No. 115,487, filed on Nov. 2, 1987, now abandoned.

FIELD OF THE INVENTION

This invention pertains to both a useful and novel drug delivery device for dispensing a drug to an environment of use. Particularly, the invention pertains to an osmotic drug-delivery device containing a controlled release drug solubility modulator that regulates the solubility of the drug(s) within the device. This regulation affects the release profile of the drug from the device. Consequently, selecting the proper drug solubility modulator allows the release of drug to be controlled by the delivery device and not by the intrinsic water solubility of the drug or the environment surrounding the device.

In the instant invention, solubility modulation of drugs is achieved through use of solubility modulating complexing agents and surfactants.

BACKGROUND OF THE INVENTION

The need for systems that can deliver a drug at a controlled rate of release to an environment of use over a specified period of time is well established.

U.S. Pat. Nos. 3,854,770 and 3,916,899 disclose devices which have semipermeable walls that are permeable to water and substantially impermeable to dissolved drugs and solutes. A passageway through the semipermeable wall, disclosed as a drilled hole, is provided as an exit portal for the drug through the wall. U.S. Pat. Nos. 4,256,108; 4,160,452; 4,200,098 and 4,285,987 disclose devices which contain multiple wall layers, at least one of said walls having a drilled hole for the release of core components through a rate-controlling semipermeable membrane that is substantially impermeable to dissolved drugs and other solutes. The use of controlled release solubility modulators that regulate the solubility of the drug(s) within the device to control drug release from the an osmotic drug-delivery device were not disclosed. U.S. Pat. No. 4,326,525 is also based on semipermeable membrane technology with a drilled hole acting as exit portal for the drug. This patent discloses the use of buffers which react via proton-transfer or neutralizing reactions with the drug to produce a new drug agent which has different thermodynamic properties from the parent drug.

U.S. Pat. No. 4,755,180 is also based on semi-permeable membrane technology with a drilled hole acting as the exit portal for the drug. This patent discloses the use of buffers and osmagents to induce control of drug solubility through manipulation of the drug pH/solubility profile or through competition for available water, that is thermodynamic alteration of the water, respectively. In all cases the drug released from the device exits as a free unassociated dissolved molecule that is solvated directly by water. This approach would be ineffective, for example, in manipulation of poorly soluble drugs with no acid/base character.

The usefulness of the above devices would be increased if a device and method were provided to improve the delivery of drugs which have been found to be difficult to incorporate into an osmotic drug delivery module without conversion of the parent drug into a new drug whose stability and toxicology are uncharacterized. Further utility results from methodology which provides for a sustaining of the improvement inducing effect through use of solubility modulating agents that are effective in the formulation of poorly water soluble drugs having no acid/base character in technology which substantially extends the lifetime of the modulating agent(s).

DESCRIPTION OF DRAWINGS

FIG. 1a is another embodiment of the instant invention where the semipermeable wall, 1, is coated with a layer of material, 8, that is soluble in fluids of the intended environment of use (commonly water), with a microporous wall, 7, separating the layer, 8, from the external environment. The compound(s) of layer, 8, dissolve and then freely permeate the microporous wall, 7, in a fluid environment, creating a fluid filled zone separating the microporous and semipermeable walls. Drug laden solution that is pumped through the hole, 6, at a rate controlled by the semipermeable wall, 1, enters the now fluid layer, 8, where it may then freely permeate the microporous wall, 7, to the exterior. All other components were defined previously.

OBJECT OF THE INVENTION

Figure 1:
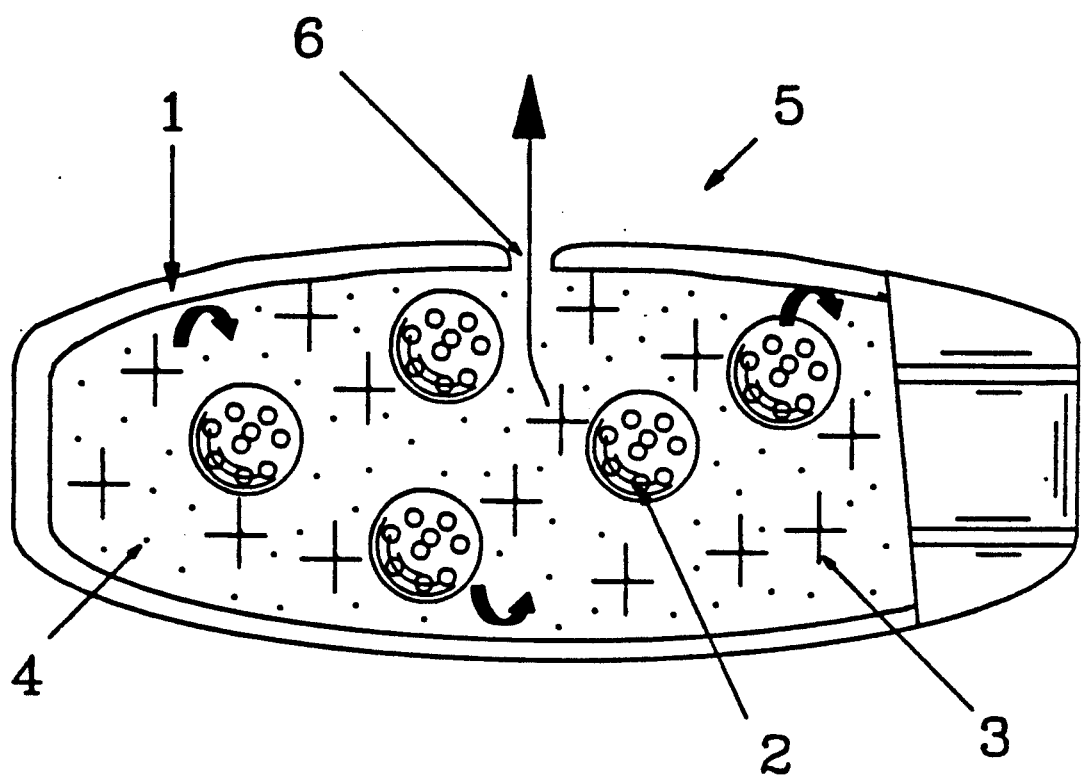
FIG. 1 is a schematic representation of one embodiment of the instant invention. The device, 5, has a core composition comprised of drug(s), 3, solubility modulator(s), 2, surrounded by a microporous membrane or dispersed throughout a matrix to form controlled release solubility modulating units that are dispersed among other excipients, 4, which may optionally contain elements found in 2, as needed to form a tablet suitable for the application of a semipermeable, rate determining, water-insoluble wall, 1. In operation water permeates wall 1 at a rate controlled by the nature of wall 1, entering the core compartment where drug and excipients dissolve. The solubility modulator(s), 2, are metered through the rate modifying microporous member or matrix into the core environment for a prolonged period where the solubility of drug, 3, is modified. A priming bolus of agent 2 may be provided in 4, to modulate the drug solubility during the lag-time for water and solution to actuate release of 2. Drug, 3, and those excipients and solubility modifiers which are dissolved in the core fluids are then freely permeable to exit the core compartment through the release means in the wall 1, exemplified here as a hole, 6, in response to osmotic and concentration gradients. It is often desirable for the lifetime of agent, 2, and drug, 3, to closely coincide to allow for solubility control throughout the entire delivery period of the drug. However, it is not a necessary requirement that the lifetimes of 2 and 3 be similar; in practice, lifetimes may be adjusted to achieve the kinetic profile of drug release best suited to the therapeutic need.
Figure 1B:
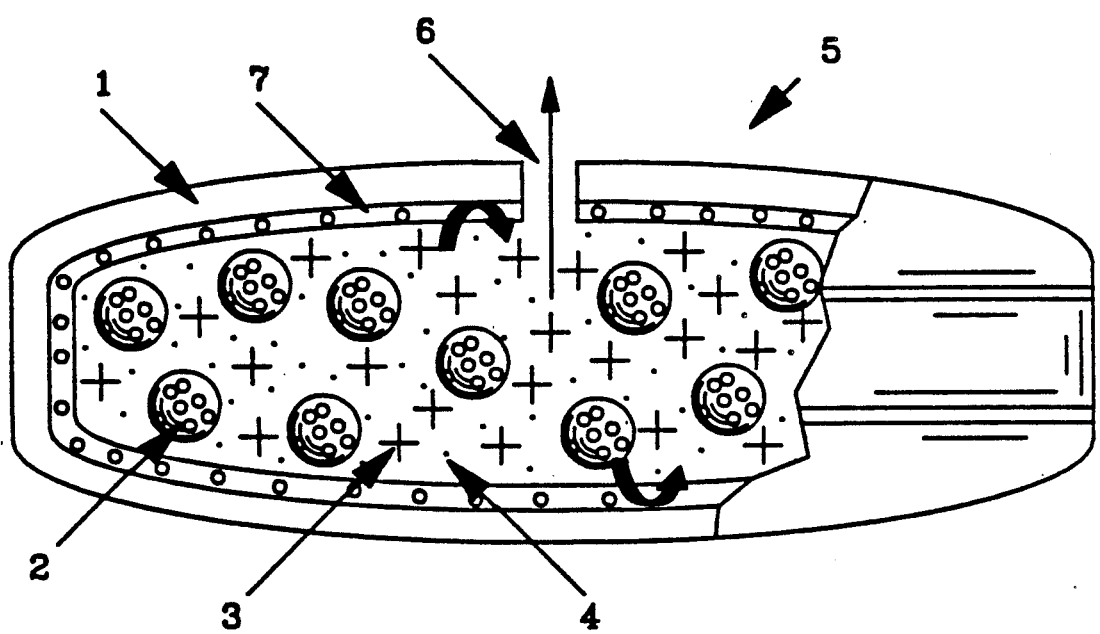
FIG. 1b is another embodiment of the instant invention. As configured, the drug containing core is coated with a laminate structure comprised of a microporous wall, 7, immediately contacting the core, and an overcoating semipermeable wall, 1. The microporous wall serves as a base coating to lend mechanical strength and support to the rate controlling semipermeable wall. A hole, 6, is provided as an exit portal for the drug solution. Other components were defined previously.

It is an immediate object of this to provide a novel device for delivering an agent (drug) to produce a beneficial effect which overcomes the disadvantages associated with prior art devices.

Another object of the invention is to provide a device for delivering an agent at controlled rate over a specified period of time, which delivery is controlled by the device and not the environment surrounding the device.

Another object of the invention is to provide a device for controlled delivery of a drug and a solubility modulating agent where the solubility, and thus delivery profile, of said drug is controlled by the drug delivery device and not by the intrinsic water solubility of the drug.

Another object of the invention is to provide a method for converting unacceptable drug release profiles into profiles that have been recognized as therapeutically desirable. For example, drugs with intrinsic water solubilities that are very low will release from osmotic devices at slow rates that may be subtherapeutic; modulation to increase the solubility of such drugs will increase the release rate into the therapeutic range. The above effects are achieved without chemical modification of the parent drug eliminating attendant stability and toxicological concerns.

Another object of the invention is to provide a drug delivery device that is readily manufacturable to deliver a pre determined dose of agent at a programmed rate from compositions of matter in the varied geometries and sizes of tablets, pellets, multi-particulates, and such related dosage forms as familiar to those skilled in the art of oral, buccal, vaginal, rectal, nasal, ocular, aural, parenteral, and related routes of administration.

Another object of the invention is to provide a drug delivery device for delivering an active agent over a range of release rates as controlled by the device.

Other objects, features and advantages of the invention will be apparent to those skilled in the art from the following detailed description of the invention, taken in conjunction with the drawings and accompanying claims.

BRIEF DESCRIPTION OF THE INVENTION

A device is disclosed for the delivery of a beneficial agent. The beneficial agent, commonly a drug, is delivered by osmotic pumping of dissolved drug, and excipients as required, at a controlled rate for a specified period to the environment surrounding the device. The solubility of the beneficial agent is controlled through the influence of a controlled release solubility modulator contained within the drug delivery device. The controlled release solubility modulator influences the release pattern of the beneficial agent. The device is comprised of (1) At least one beneficial agent which can be poorly water soluble; and (2) A controlled release solubility modulator selected from the group consisting of surfactants and/or complexing agents which increase drug solubility. The controlled released solubility modulator can be either
  (i) surrounded by a water insoluble microporous membrane coating containing pore forming additives dispersed throughout said microporous membrane or
  (ii) dispersed in an individual matrix substrate. Components (1) and (2) may be combined with excipients, binders, lubricants, glidants, and bulking agents as need to form a core compartment of the device. The core is surrounded by a water insoluble semi-permeable wall. In operation water is imbided into the core compartment. As water enters the core it is further imbided into the compartments containing the controlled released solubility modulator. The contents of the solubility modulator compartments are delivered into the core environment where they modulate the solubility of the beneficial agent, thereby controlling the release of the beneficial agent from the device. By adjusting the amount and/or type of solubility modulator, the amount and/or type of microporous membrane or matrix applied to the solubility modulator, or amount and type of coating applied to the core compartment, the release profile of the device can be adjusted to give the desired kinetic profile.

DETAILED DESCRIPTION OF THE INVENTION

The instant invention is directed to a drug-delivery device for the controlled release of a therapeutically active ingredient into an environment of use which comprises:

A. a plurality of controlled release solubility modulating units comprised of core composition comprising
  (a) a solubility modulating agents each of which is a complexing agent or a surfactant and which is either (i) surrounded by a water insoluble coat containing at least one pore forming additive dispersed throughout said coat, or (ii) dispersed in an individual matrix substrate, and
  (b) a diffusible therapeutically active ingredient; and
B. a water insoluble wall surrounding said core composition and prepared from a semipermeable material substantially impermeable to core composition and permeable to the passage of an external fluid in the environment of use, with said wall having a means for release of the therapeutic agent through the water insoluble wall.

Other walls, such as microporous walls, and soluble layers that are freely permeable to dissolved solutes may be incorporated in conjunction with the semipermeable wall.

The term "solubility modulating agent" as described herein encompasses any surfactant or complexing agent that can exert an effect on the water solubility of the drug being delivered from the device without chemical modification of the drug. Complexation is a method for solubility modulation useful in the present invention. Complexes may be classified as metal ion complexes, organic molecular complexes, and inclusion compounds. Specific examples of complexing agents include but are not limited to sodium mandelate, 2 hydroxyphenyl acetic acid, 2-hydroxynicotinic acid, 3-hydroxy 3-phenyl propionic acid, phthalic acid, 3-4-dihydroxycinnamic acid cyclodextrins, polyethylene glycols, polyvinylpyrrolidone, sodium carboxymethylcellulose, tetracycline derivatives, caffeine, picric acid, quinhydrone, hydroquinone sodium salicyate, salicylic acid, mandelic acid, and the like, and bile salts and acids Another group of solubility modulating agents are surfactants. Generally, the surfactants are amphipathic molecules comprised of a hydrophobic part and a hydrophilic part. The surfactants can be anionic, cationic, non-ionic or amphoteric. The anionic surfactants include sulfated, sulfonated, or carboxylated esters, amides, alcohols, ethers, aromatic hydrocarbons, aliphatic hydrocarbons, acylated amino acids and peptides. Metal aklyl phosphates are another class of anionic surfactants. Typically, cationic surfactants are primary, secondary, tertiary or quaternary alkylammonium salts, acylated polyamines and salts of heterocyclic amines. Non-ionic surfactants are typically esters and ethers of polyoxyalkene glycols, polyhydric alcohols, or phenols. Poloxamers and poloxamines are included as non-ionic surfactants. Surfactants are discussed in *Surfactants Systems, Their Chemistry, Pharmacy and Biology*, D. Attwood and A. T. Florence, Chapman and Hall Pub. Co. 1983. Examples of surfactants include potassium laurate, sodium alkylsulfates such as sodium dodecyl sulfate, hexadecyl sulphonic acid, and sodium dioctylsulphosuccinate, hexadecyl(cetyl)trimethylammonium bromide, dodecylpyridinium chloride, dodecylamine hydrochloride, N-dodecyl-N,N-dimethyl betaine, bile acids and salts, acacia, tragacanth, Igepal (polyoxyethylated nonylphenols), sorbitan esters (Spans), polysorbates (Tweens), Triton-X analogs (polyoxyethylated t-octylphenols), Brij analogs selected from the group consisting of polyoxyethylene lauryl ethers, polyoxyethylene cetyl ethers, polyoxyethylene stearyl ethers, and polyoxyethylene oleyl ethers, Myrj analogs (polyoxyethylene stearates), pluronics and tetronics selected from the group consisting of poloxamer and poloxamine type polyoxyethylene-polyoxypropylene derivatives, surface active drug agents such as phenothiazines and tricyclic antidepressants, and the like.

The solubility modulating agent can be surrounded by a water insoluble, microporous membrane that contains at least one pore forming additive dispersed throughout said microporous membrane. This membrane is often applied to the solubility modulating agent by spray-coating procedures. A portion of the solubility modulating agent may be left uncoated to effect immediate availability during the period intervening the onset of release from the controlled release solubility modulating element(s). The solubility modulating agent can also be incorporated into individual matrix units, incorporation effects a controlled release of said agent. Other excipients may also be combined with the beneficial agent (drug) and solubility modulating agent(s) as needed to maintain pH, promote stability, facilitate manufacturability, and provide osmotic activity to the dissolved core compartment solution to effect a desirable release profile. The entire composite is compressed or formed into tablets, beads, multi particulates, and the like, by conventional methodology to form cores onto which a water insoluble wall containing leachable pore forming additives is applied. Thus, the finished device may contain solubility modulators in the various forms of either: (a) microporous membrane solubility modulator; (b) solubility modulator dispersed in a matrix; (c) immediate release solubility modulator; or; (d) a mixture of (a), (b), and (c) within the core compartment which is then surrounded by a semipermeable wall.

The core compartment containing the water soluble drug and solubility modulator, as described herein, is typically in the form of a solid conventional tablet, pellet or particulate. The core is completely encased by the semipermeable wall. The core can be comprised of a mixture of agents combined to give the desired manufacturing and delivery characteristics. The number of agents that may be combined to make the core is substantially without an upper limit with the lower limit equalling two components.

The preferred specifications for the core are summarized below and include:

1. Core Drug Loading (size): 0.05 nanograms to 5 grams or more (includes dosage forms for humans and animals).

2. Osmotic pressure developed by a solution of the core: 8 to 500 atmospheres, typically, with commonly encountered drugs and excipients; however osmotic pressures greater than zero are within guidelines.

3. Core solubility: continuous, uniform release (zero-order kinetics) of 90% or greater of the initially loaded core mass is theoretically predicted if the ratio of the dissolvable core mass solubility, S, to the dissolvable core mass density, $\rho$, that is $S/\rho$, is 0.1 or lower. Typically this occurs when 10% of the initially loaded dissolvable core mass saturates a volume of external fluid equal to the total volume of the initial dissolvable core mass.

$S/\rho$ ratios greater than 0.1 fall within the workings of the invention and result in lower percentages of initial core mass delivered under zero-order kinetics $S/\rho$ can be selected to give acceptable combined characteristics of stability, release rate, and manufacturability.

4. Controlled Release Solubility Modulator: 0.01 to 75% by weight of the total core mass.

In cases where the drug and the solubility modulating agent exhibit the desired solubility, osmotic pressure, density, stability, and manufacturability characteristics, there is no critical upper limit as to the amount of drug that can be incorporated into a core mass and typically will follow the core loading (size) specification 1. The lower limit ratio of drug to excipient is dictated by the desired drug solubility desired osmotic activity of the core composition, the desired time span and profile of release, and the pharmacological activity of the drug. Generally the core will contain 0.01% to 90% by weight or higher, of an active agent in mixture with other solute(s). Representative of compositions of matter that can be released from the device and can function as a solute are, without limitation, those compositions soluble in fluids inside the core compartment as described.

The expressions drug, beneficial agent, and therapeutically active agent as used herein broadly includes any compound, or mixture thereof, that can be delivered from the system to produce a beneficial result. The drug can be soluble in fluid that enters the reservoir and functions as an osmotically effective solute or it can have limited solubility in the fluid and be mixed with an osmotically effective solute(s) that is soluble in fluid that is delivered from the system. The term drug includes pesticides, herbicides, germicides, biocides, algicides, rodenticides, fungicides, insecticides, antioxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, and other agents that benefit the environment of use.

In the specification and the accompanying claims, the terms drug, beneficial agent and therapeutically active agent include any physiologically or pharmacologically active substances that produce a localized or systemic effect or effects in animals, which term includes mammals, humans and primates. The term also includes domestic household, sport or farm animals such as sheep, goats, cattle, horses and pigs, for administering to laboratory animals such as mice, rats and guinea pigs, and to fishes, to avians, to reptiles and zoo animals. The term "physiologically" as used herein denotes the administration of drug to produce desirable levels and functions. The term "pharmacologically" denotes the study of the actions of drugs on living systems, including therapeutics, as defined in *Dorland's Illustrated Medical Dictionary*, 1974, Published by W. B. Sanders Co., Philadelphia, PA. The phrase drug formulation as used herein means the drug and solubility modulating agent in the compartment, or the drug and solubility modulating agent in the compartment mixed with an osmotic solute, binder, buffer, dye, mixtures thereof, and the like. The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synaptic sites, neuroeffector junctional sites, endocrine and hormone systems, immunological system, reproductive system, skeletal system, autocoid systems, alimentary and excretory systems, inhibitory or autocoids and histamine systems, and those materials that act on the central nervous system such as hypnotics and sedatives.

Examples of beneficial drugs are disclosed in *Remington's Pharmaceutical Sciences*, 17th Ed., 1985, published by Mack Publishing Co., Eaton, Pa.; and in *The Pharmacological Basics of Therapeutics*, by Goodman and Gilman, 6th Ed., 1980, published by the MacMillan Company, London; and in *The Merck Index*, 10th Edition, 1983, published by Merck & Co., Rahway, N.J. The drug can be in various forms, such as neutral or charged molecules, neutral or charged molecular complexes or associations or ionizable salts. Acceptable salts include, but are not limited to hydrochlorides, hydrobromide, sulfate, laurylate, palmitate, phosphate, nitrate, borate, acetate, maleate, tromethamine, tartrate, oleate, salicylate, salts of metals, and amines or organic cations, for example quaternary ammonium.

Derivatives of drugs such as esters, ethers and amides which have ionization and solubility characteristics suitable for use herein can be used alone or mixed with other drugs which upon release from the device, is converted by enzymes, hydrolyzed by body pH or other metabolic processes to the original form, or to a biologically active form.

Specific examples of drugs that may be adapted for use include sulindac, diflunisal, prostaglandins, ivermectin, avernectubsm dexanethasone, norethindrone, norgestrel, ethinylestradiol, hydrochlorothiazide, timolol, norlfoxacin, theophylline, haloperidol, digoxin, nifedipine, enalapril, lisinopril, ranitidine, famotidine, lovastatin, pravastatin, simvastatin and milbemycins, diazepam, levodopa/carbidopa, L-methyldopa, and indomethacinl. The above list of drugs is not meant to be exhaustive. Many other drugs will certainly work in the instant invention.

The drug can be in the core compartment as a solution, dispersion, paste, cream, particle, granule, emulsion, suspension or powder. Also, the drug can be mixed with a binder, dispersant, emulsifier or wetting agent and dyes.

The amount of drug is generally initially in excess of the amount that can be dissolved in the fluid that enters the reservoir. Generally, the device can house from 0.5 ng to 5 gms or more, with individual devices containing, for example, 25 ng, 1 mg, 5 mg, to 50 mg, 500 mg 1.5 mg and the like.

The core compartment containing the drug and the controlled release solubility modulator, as described herein, is typically in the form of a solid conventional tablet, pellet or particulate. The core can be comprised of a mixture of agents combined to give the desired manufacturing and delivery characteristics. The number of agents that may be combined to make the core is substantially without an upper limit with the lower limit equalling two components. It may be useful to buffer the core compartment to control the electrostatic charge of the drug.

The rate controlling wall of the invention that surrounds the core is comprised of a material that is semi permeable, can form films, and does not adversely affect the drug, animal body, or host, for example, a material that is permeable to an external fluid such as water and the like while essentially impermeable to a selected product, drugs, modulating agents, or to other compounds in the device. The selectively permeable material or membrane forming the wall is insoluble in body fluids and non-erodible or it can be bioerodible after a predetermined period with bioerosion corresponding to the end of the active drug release period. In each instance it is semipermeable to solvent but not to solute(s) and is suitable for construction of the osmotic powered device. Typical materials for forming the wall include membranes known to the art as osmosis and reverse osmosis membranes. Generally, membranes having a fluid permeability of 0.01 to 10 cc/cm$^2$ X hour or day/or higher at atmospheric pressure against a saturated product solution or saturated solute solution at the temperature of use while simultaneously possessing a high degree of impermeability to the product or solute are useful for manufacturing the devices of the invention. Of course, other semi permeable membranes operable for the purposes of the invention can also be used within the spirit of the invention.

Additional, preferred specifications for the semipermeable wall include:

1. Plasticizers and Flux Regulating Additives: 0 to 50, preferably 0.001 to 50, parts per 100 parts wall material.

2. Surfactant Additives: 0 to 40, preferably 0.001 to 40, parts per 100 parts wall material.

3. Wall Thickness: 1 to 1,000, preferably 20 to 500, microns typically, although thinner and thicker fall within the invention.

Any polymer permeable to water but impermeable to solutes as previously defined may be used. Examples include cellulose acetate having a degree of substitution, D.S., meaning the average number of hydroxyl groups on the anhydroglucose unit of the polymer replaced by a substituting group, up to 1 and acetyl content up to 21%; cellulose diacetate having a D.S. of 1 to 2 and an acetyl content of 21 to 35%; cellulose triacetate having a D.S. of 2 to 3 and an acetyl content of 35 and 44.8%; cellulose propionate having a acetyl content of 1.5 to 7% and a propionyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate having an acetyl content of 2 to 99.5%, a butyryl content of 17 to 53%, and a hydroxyl content of 0.5 to 4.7%; cellulose triaceylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose dicaprylate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional polymers that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate, methylcyanoethyl cellulose, cellulose acetate methoxyacetate, cellulose acetate ethoxyacetate, cellulose acetate dimethylsulfamate, ethylcellulose, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose stearate, cellulose acetate methylcarbamate, agar acetate, amylose triacetate, beta glucan acetate, beta glucan triacetate, acetaldehyde dimethyl acetate, cellulose acetate ethyl carbamate, cellulose acetate phthalate, cellulose acetate dimethyl aminoacetate, cellulose acetate ethyl carbonate, poly (vinyl methyl) ether copolymers, cellulose acetate with acetylated hydroxyethylcellulose, cellulose, hydroxylated ethylenevinylacetate, poly(ortho ester)s, polyacetals, semipermeable polyglycolic or polylactic acid and derivatives thereof, film forming materials with a water sorption of one to fifty percent by weight at ambient temperatures with a presently preferred water sorption of less than thirty percent, acylated polysaccharides, acylated starches, aromatic nitrogen containing polymeric materials that exhibit permeability to aqueous fluids, membranes made from polymeric epoxides, copolymers of alkylene oxides and alkyl glycidyl ethers, polyurethanes, polyacrylate and polymethacrylate polymers, and derivatives and the like. Admixtures of various polymers may also be used.

The polymers described are known to the art or they can be prepared according to the procedures in *Encyclopedia of Polymer Science and Technology*, Vol. 3, pages 325 to 354, and 459 to 549, published by Interscience Publishers, Inc., New York, in *Handbook of Common Polymers* by Scott, J. R. and Roff, W. J., 1971, published by CRC Press, Cleveland, Ohio; and in U.S. Pat. Nos. 3,133,132; 3,276,586; 3,541,055; 3,541,006; and 3,546,142.

The expression "release means" or hole(s) as used herein is comprised of those means and methods suitable for osmotically releasing the drug from the core through the semipermeable wall.

The expression includes the following: an aperture, orifice, bore, porous element through which product can migrate, hollow cellulose acetate fibers suitable for passing the drug, capillary tubes, cracks, and the like. The expression also includes bioerodible materials that erode in the environment of use to produce an osmotic passageway of precontrolled dimensions. Typical bioerodible materials suitable for forming a passageway include erodible poly(glycolic) acid and poly(lactic) acid fibers, poly(ortho esters), erodible gelatinous filaments, poly(vinyl alcohol), and the like.

The water insoluble, permeable, microporous walls may be applied to core composition masses prior to the application of the semipermeable wall or subsequent thereto by spray coating procedures. The microporous wall may either directly contact the semipermeable wall to form a bilaminate structure, or, the microporous wall may be separated from the semipermeable wall by a layer of fluid soluble material, which may optionally contain drug, which dissolves in the environment of use, creating a fluid layer separating the microporous and semipermeable walls. This microporous wall is comprised of (a) polymeric material that is insoluble in the fluids of the environment of intended use (usually water), (b) other added excipients that will dissolve in the environmental fluids or leach out of the wall. The leached wall is a sponge like structure composed of numerous open and closed cells that form a discontinuous interwoven network of void spaces when viewed with a scanning electron microscope. The wall is permeable to both water and solutes, and as constituted in the environment of use has a small solute reflection coefficient, $\sigma$ and displays poor semipermeable characteristics when placed in a standard osmosis cell. Additional specifications for the microporous wall include:

1. Wall Thickness: 1 to 1,000, preferably 20 to 500, microns typically although thinner and thicker fall within the invention.

2. Pore Forming Additives: 0.1 to 100%, preferably 0.1 to 75%, by weight, based on the total weight of pore forming additive and polymer, pore forming additive, preferably: (a) 0.1 to 50% by weight solid additive; (b) 0.1 to 40% by weight liquid additive.

A microporous wall can be generically described as having a sponge-like appearance. The pores can be continuous pores that have an opening on both faces of a microporous lamina, pores interconnected connected through tortuous paths of regular and irregular shapes including curved, curved-linear, randomly oriented continuous pores, hindered connected pores and other porous paths discernible by microscopic examination. Generally, microporous lamina are defined by the pore size, the number of pores, the tortuosity of the microporous path and the porosity which relates to the size and number of pores. The pore size of a microporous lamina is ascertained by measuring the observed pore diameter at the surface of the material under the electron microscope. Generally, materials possessing from 5% to 95% pores and having a pore size of from 10 angstroms to 100 microns can be used.

Pore forming additives may be used in the instant invention. The microporous wall may be formed in situ, by a pore former being removed by dissolving or leaching it to form the microporous wall during the operation of the system. The pores may also be formed in the wall prior to operation of the system by gas formation within curing polymer solutions which result in voids and pores in the final form of the wall. The pore-former can be a solid or a liquid. The term liquid, for this invention embraces semi solids, and viscous fluids. The pore-formers can be inorganic or organic. The pore formers suitable for the invention include pore formers that can be extracted without any chemical change in the polymer. Solid additives include alkali metal salts such as sodium chloride, sodium bromide, potassium chloride, potassium sulfate, potassium phosphate, sodium benzoate, sodium acetate, sodium citrate, potassium nitrate and the like; the alkaline earth metal salts such as calcium chloride, calcium nitrate, and the like; the transition metal salts such as ferric chloride, ferrous sulfate, zinc sulfate, cupric chloride, and the like. Water may be used as the pore-former. The pore-formers include organic compounds such as dimethyl sulfone, nicotinamide, tromethamine, saccharides and amino acids. The saccharides include the sugars sucrose, glucose, fructose, mannose, galactose, aldohexose, altrose, talose, lactose, monosaccharides, disaccharides, and water soluble polysaccharides. Also, sorbitol, pentaerythritol, mannitol, organic aliphatic and aromatic ols, including diols and polyols, as exemplified by polyhydric alcohols, poly(alkylene glycols), polyglycols, alkylene glycols, poly($\alpha$, $\omega$) alkylenediols esters or alkylene glycols, polyvinylalcohol, poly vinyl pyrrolidone, and water soluble polymeric materials. Pores may also be formed in the wall by the volatilization of components in a polymer solution or by chemical reactions in a polymer solution which evolves gases prior to application or during application of the solution to the core mass resulting in the creation of polymer foams serving as the porous wall of the invention. The pore-formers are nontoxic, and on their removal channels are formed that fill with fluid. The channels become a transport path for fluid. In a preferred embodiment, the non toxic pore forming agents are selected from the group consisting of water soluble inorganic and organic compounds and salts, carbohydrates, polyols, polyalkylene glycols, poly($\alpha$, $\omega$) alkylenediols, esters of alkylene glycols, and glycols, that are used in a biological environment.

The microporous materials can be made by etched nuclear tracking, by cooling a solution of flowable polymer below the freezing point with subsequent evaporation of solvent to form pores, by gas formation in a polymer solution which upon curing results in pore formation, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes: A Structural Perspective*, 2nd Ed., by R. E. Kesting, Chapters 7 and 8, 1985, published by John Wiley & Sons, Inc.; *Chemical Reviews*, Ultrafiltration, Vol. 18, pages 373 to 455, 1934; *Polymer Eng. and Sci.*, Vol. 11, No. 4, pages 284 to 288, 1971, *J. Appl. Poly. Sci.*, Vol. 15, pages 811 to 829, 1971, and in U.S. Pat. Nos. 3,565,259; 3,615,024; 3,751,536; 3,801,692; 3,852,224; and 3,849,528.

It is generally desirable from a preparation standpoint to mix the polymers which will comprise either the semipermeable or microporous walls in a solvent. Exemplary solvents suitable for manufacturing the wall of the instant device include inert inorganic and organic solvents that do not adversely harm the core, wall, and the materials forming the final wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl ethyl ketone, methyl propyl ketone, n-hexane, ethyl lactate, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, dimethylbromamide, benzene, toluene, naphtha, 2,4-dioxane, tetrahydrofuran, diglyme, water, and mixtures thereof such as acetone and water, acetone and methanol, acetone and ethyl alcohol, methylene dichloride and methanol, and ethylene dichloride and methanol. Illustrative of mixed solvents are acetone methanol (80:20), acetone ethanol (90:10), methylene dichloride-methanol (80:20), ethyl acetate ethanol (80:20), ethylene dichloride-methanol (80:20), methylene dichloridemethanol (50:50), methylene dichloride-methanol (78:22), acetone-water (90:10), chloroform-ethanol (80:20), methylene dichloride-ethanol (79:21), methylene chloride-methanol-water (15:10:1), carbon-tetrachloride-methanol (70:30), expressed as (weight:weight), and the like. Water based latex forms of suitable polymers are also within the guidelines of the invention.

Exemplary plasticizers suitable for the present wall forming purposes include plasticizers that lower the temperature of the second-order phase transition of the wall or the elastic modulus thereof, and also increase the workability of the wall and its flexibility. Plasticizers may increase or decrease the permeability of the wall to fluids including water and aqueous solutions. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, polyethylene glycols, polypropylene glycols, and halogenated phenyls. Generally, from 0.001 to 50 parts of a plasticizer or a mixture of plasticizers are incorporated into 100 parts of wall forming material.

Exemplary plasticizers include dialkyl phthalates, dicycloalkyl phthalates, diaryl phthalates and mixed alkylaryl as represented by dimethyl phthalate, dipropyl phthalate, dioctyl phthalate, di-(2-ethyl-hexyl)-phthalate, di-isopropyl phthalate, diamyl phthalate and dicapryl phthalate; alkyl and aryl phosphates such as triethyl phosphate, tributyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di-(2-methoxyethyl)-adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol dibutyrate and triethylene glycol dipropionate. Other plasticizers include polyethylene glycol 400, polyethylene glycol 20,000, camphor, N-ethyl-(o and p-toluene) sulfonamide, chlorinated biphenyl, benzophenone, N-cyclohexyl-p-toluene sulfonamide, and substituted epoxides.

Suitable plasticizers can be selected for blending with the wall forming materials by selecting plasticizers that have a high degree of solvent power for the materials, are compatible with the materials over both the processing and use temperature range, exhibit permanence as seen by their tendency to remain in the plasticized wall, impart flexibility to the material and are non toxic to animals, humans, avians, fishes and reptiles. Procedures for selecting a plasticizer having the described characteristics are disclosed in the *Encyclopedia of Polymer Science and Technology*, Vol. 10, pages 228 to 306, 1969, published by John Wiley & Sons, Inc. Also, a detailed description pertaining to the measurement of plasticizer properties including solvent parameters and compatibility such as the Hildebrand solubility parameter $\delta$, the Flory-Huggins interaction parameter $\chi$, and the cohesive energy density, CED, parameters are disclosed in *Plasticization and Plasticizer Processes*, Advances in Chemistry Series 48, Chapter 1, pages 1 to 26, 1965, published by the American Chemical Society. The amount of plasticizer added generally is an amount sufficient to produce the desired wall and it will vary according to the plasticizer and the other wall forming materials. Usually about 0.001 part up to 50 parts of plasticizer can be used for 100 parts of wall material.

The expressions "flux regulator agent", "flux enhancing agent" and "flux decreasing agent" as used herein mean a compound that when added to a wall forming material assists in regulating the fluid permeability (flux) through the wall. The agent can be preselected to increase or decrease the fluid flux. Agents that produce a marked increase in permeability to a fluid such as water, are often essentially hydrophilic, while those that produce a marked decrease in permeability to fluids such as water, are often essentially hydrophobic. The flux regulators in some embodiments also can increase the flexibility and porosity of the lamina. Examples of flux regulators include polyhydric alcohols and derivatives thereof, such as polyalkylene glycols of the formula $H-(O-alkylene)_n-OH$ wherein the bivalent alkylene radical is straight or branched chain and has from 1 to 10 carbon atoms and n is 1 to 500 or higher. Typical glycols include polyethylene glycols 300, 400, 600, 1500, 1540, 4000 and 6000 of the formula $H-(OCH_2CH_2)_n-OH$ wherein n is typically 5 to 5.7, 8.2 to 9.1, 12.5 to 13.9, 29 to 36, 29.8 to 37, 68 to 84, and 158 to 204, respectively. Other polyglycols include the low molecular weight glycols of polypropylene, polybutylene and polyamylene.

Additional flux regulators include poly ($\alpha$, $\omega$) alkylenediols wherein the alkylene is straight or branched chain of from 2 to 10 carbon atoms such as poly(1,3)-propanediol, poly(1,4) butanediol, poly(1,5)pentanediol and poly(1,6)hexanediol. The diols also include aliphatic diols of the formula $HOC_nH_{2n}OH$ wherein n is from 2 to 10 and diols are optionally bonded to a non terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula $HO-(alkylene-O)_n-H$ wherein the divalent alkylene radical includes the straight chain groups and the isomeric forms thereof having from 2 to 6 carbons and n is 1 to 14. The esters and polyesters are formed by reacting the glycol with either a monobasic or dibasic acid or anhydride. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid, and polyester of triethylene glycol with adipic acid.

The amount of flux regulator added to a material generally is an amount sufficient to produce the desired permeability, and it will vary according to the lamina forming material and the flux regulator used to modulate the permeability. Usually from 0.001 parts up to 50 parts, or higher of flux regulator can be used to achieve the desired results.

Surfactants useful for the present wall forming purpose are those surfactants, when added to a wall forming material and other materials, aid in producing an integral composite that is useful for making the operative wall of a device. The surfactants act by regulating the surface energy of materials to improve their blending into the composite. The composite material is used for manufacturing devices that maintain their integrity in the environment of use during the agent release period. Generally, the surfactants are amphipathic molecules comprised of a hydrophobic part and a hydrophilic part. The surfactants can be anionic, cationic, nonionic or amphoteric. The anionic surfactants include sulfated, sulfonated, or carboxylated esters, amides, alcohols, ethers, aromatic hydrocarbons, aliphatic hydrocarbons, acylated amino acids and peptides. Metal alkyl phosphates are another class of anionic surfactant. Typically, cationic surfactants are primary, secondary, tertiary or quaternary alkylammonium salts, acylated polyamines, and salts of heterocyclic amines. Nonionic surfactants are typically esters and ethers of polyoxyalkylene glycols, polyhydric alcohols, or phenols. Poloxamers are included as nonionic surfactants. Ampholytic molecules such as betaine are also surfactants. Surfactants are discussed in *Surfactant Systems, Their Chemistry, Pharmacy, and Biology*, D. Attwood and A. T. Florence, Chapman and Hall Pub. Co., 1983, pgs 1-8.

Suitable surfactants can be selected for blending with wall forming materials by using the surfactant's hydrophile lipophile balance number, HLB. This number represents the proportion between the weight percentages of hydrophilic and lipophilic groups in a surfactant. In use, the number indicates the behavior of the surfactant, that is, the higher the number the more hydrophilic the surfactant and the lower the number the more lipophilic the surfactant. The required HLB number for blending wall forming materials is determined by selecting a surfactant with a known HLB number, blending it with the materials and observing the results. A uniform composite is formed with the correct HLB number, while a non-uniform mixture indicates a different number is needed. This new number can be selected by using the prior HLB number as a guide. The HLB number is known to the art for many surfactants, and they can be experimentally determined. Generally a HLB number of 10 or less indicates lipophilic behavior and 10 or more indicates hydrophilic behavior. Also, HLB numbers are algebraically additive. Thus, by using a low number with a high number, blends of surfactant can be prepared having numbers intermediate between the two numbers. The concept of HLB is detailed in *Remington's Pharmaceutical Sciences*, 16th Ed., Mack Pub. Co., (1980), pages 316-319. The amount of surfactant needed is an amount that when blended with wall forming materials will form the desired wall composite, and it will vary according to the particular surfactant and materials that are blended to form the wall. Generally, the amount of surfactant will range from about 0.001 part up to 40 parts for 100 parts of wall.

The layer of fluid soluble material which may be positioned between a semipermeable wall containing a hole(s) and a microporous wall, comprises a layer of material selected from organic or inorganic compounds that are soluble in the fluid of the environment of use; drug may optionally be included. Fluid entering the system (commonly water) dissolves the layer to form a solution which is released to the exterior through the microporous wall. Drug laden solution exiting the hole(s) in the semipermeable wall enters this fluid layer at a rate controlled by the semipermeable wall from where the drug is released to the exterior through the microporous wall. Representative inorganic compounds that can be used for forming the layer include magnesium chloride, sodium chloride, lithium chloride, potassium chloride, sodium carbonate, potassium carbonate, manganese carbonate, sodium sulfite, potassium sulfite, lithium sulfite, magnesium sulfate, calcium bicarbonate, sodium bicarbonate, potassium bicarbonate, sodium sulfite, potassium sulfite, lithium sulfite, magnesium sulfite, potassium acid phosphate, sodium acid phosphate, and the like. Typical organic compounds include carbohydrates such as glucose, sucrose, fructose, raffinose and lactose, and other organic compounds soluble in water and biological fluids such as sorbitol, mannitol, inositol, urea, magnesium succinate, tartaric acid, tromethamine and the like.

The following examples illustrate the preparation of the drug delivery devices of this invention and their controlled release of one or more therapeutically active ingredients into an environment of use and as such are not to be considered as limiting the invention set forth in the claims appended hereto.

EXAMPLES

In the following examples the hydroxymethyl-glutaryl-coenzyme A reductase inhibitors (HMG CoA reductase inhibitors) simvastatin and lovastatin are used as model drugs. These drugs are highly effective in the reduction of blood cholesterol levels in humans and possess neither acidic nor basic functionality. The aqueous solubilities of simvastatin and lovastatin are 0.03 mg/ml and 0.00044 mg/ml respectively, at 20° C. Their very low water solubilities would preclude the incorporation of these drugs into conventional osmotic controlled release drug-delivery devices. The solubility modulating properties of surfactants and complexing agents to increase the total solubilities of simvastatin and lovastatin are disclosed. This permits the successful formulation of poorly water soluble drugs into controlled-release osmotic drug-delivery devices.

EXAMPLE 1

A plurality of solubility modulated osmotic drug-delivery devices containing controlled release sodium dodecyl sulfate (C.R. SDS) surfactant particles to modulate the solubility of simvastatin are prepared. The C.R. SDS is manufactured by first granulating 300 g lactose mixed with 300 g SDS in a fluid-bed granulator to form SDS granules. The granulating fluid consists of 36 g polyvinyl-pyrrolidone 29-32 k dissolved in 100 ml of ethanol. The SDS granules are dried in a convection oven at 50° C. These granules are sized through a #18 sieve (1.0 mm opening) and a microporous wall is then applied to these granules by standard fluidized-bed spray coating techniques. The microporous coat spray solution is cellulose acetate butyrate 381-20 (100 grams) dissolved in an acetone:methanol (3:1) solvent blend. To this is added 50 g sorbitol as a pore former dissolved in a methanol:water (3:1) solvent based. This solution is sprayed onto the SDS granules in a commercial Uni-glatt ® fluidized-bed coating machine. The SDS granules are coated to a thickness sufficient to give 4-24 hours of continuous release of SDS into 37° C. water as measured by a January PCM3 conductivity meter. Next, a wet granulation is prepared containing simvastatin, mannitol, sodium dodecyl sulfate, and C.R. SDS mixed 1:10:1.5:2.5. The granulating fluid consists of 9% w/w polyvinylpyrrolidone 29-32K dissolved in ethanol. The granules are dried in a convection oven at 40° C. These granules are formed into core tablets by compressing 330 mg aliquots (20 mg drug load) into a ⅜" deep concave tableting die on a manesty tablet press. Next, a semipermable coat is applied to these cores. 72 g cellulose acetate having an acetyl content of 39% and 80 g cellulose acetate having an acetyl content of 32% were dissolved in a dichloromethane/methanol solvent blend. The composite solution contained water methanol: dichloromethane in an approximate 1:10:15 ratio. This solution is sprayed onto the cores in a commercial Uni-Glatt ® fluidized-bed coating machine. A wall 100 microns thick is applied to the tablet cores and a hole 0.15 mm in diameter is drilled through the wall. The simvastatin release from these devices in vitro into 900 ml volumes of 37° C., pH 7.4 phosphate buffer made isotonic with NaCl, can be monitored in a USP Dissolution Method #2 apparatus with constant stirring at 50 rpm. HPLC can be used to assay for simvastatin.

EXAMPLE 2

The procedures outlined in Example 1 for preparation of core tablets are repeated with the exception that the C.R. SDS particles are manufactured as a matrix rather than as coated particules. The C.R. SDS matrix particles are prepared by granulating 300 g SDS with 300 g lactose. The granulating fluid consists of Methocel K4M-Premium ® (hydroxypropylmethylcellulose) dissolved in a water:ethanol solvent blend. These granules are dried in a convection oven at 50° C. The resulting C.R. SDS matrix particles release sodium dodecyl sulfate (SDS) for an extended period which may be increased through increases in the weight percent ratio of Methocel K4M-Premium ® to SDS/lactose. Next, a semi-permeable coat is applied to these tablet cores. 54 g of cellulose acetate having an acetyl content of 39% and 18 g of cellulose acetate having an acetyl content of 32% is dissolved in a dichlormethane/methanol solvent blend. To this is added 4.4 g polyethylene glycol 400 as a flux enhancer/plasticizer in a water/methanol solvent blend. The composite solution contains water:methanol:dichloromethane in an approximate 1:10:15 ratio. This solution is sprayed onto the cores in a commercial Uni-Glatt ® fluidized bed coating machine. A wall 100 microns thick is applied and a hole 0.15 mm in diameter is drilled through the wall.

EXAMPLE 3

A plurality of solubility modulated osmotic drug-delivery systems containing controlled release sodium salicylate (complexing agent) particles to modulate the solubility of lovastatin are prepared. The controlled release sodium salicylate (C.R. NaSal) is manufactured by granulating a 700 g of aliquot of sodium salicylate in a fluidized-bed granulator. The granulating fluid consists of 36 g polyvinylpyrrolidione 29–32K dissolved in 100 ml of ethanol. The granules are dried in a convection oven at 50° C. These granules are then sized through a #18 sieve (1.0 mm opening) and a microporous wall is then applied to these granules by standard fluidized-bed spray coating techniques. The spray solution is 100 g of cellulose acetate butyrate 381-20 dissolved in a 2:1 acetone:methanol solvent blend. To this is added 50 g sorbitol as a pore former in a methanol:water (3:1) solvent blend. This solution is then sprayed onto the sodium salicylate granules in a commercial Uni-Glatt ® fluidized-bed coating machine. The sodium salicylate granules are coated to a thickness sufficient to give 4–24 hours of continuous release of sodium salicylate into water (37° C.) as measured by HPLC. Next, a wet granulation is prepared containing lovastatin, sodium salicylate and C.R. NaSal mixed 1:2.5:1.25. The granulating fluid consists of 5% w/w polyvinylpyrrolidone 29–39K dissolved in ethanol. These granules are dried in a convection oven at 45° C. This mixture of granules is lubricated with 0.5% by weight magnesium stearate and compressed into 200 mg core tablets (40 mg lovastatin) in a ¼" standard concave tableting die on a Manesty ® tablet press.

The cores are coated with a semipermeable wall 100 microns thick containing a drilled 0.15 mm diameter hole as described in Example 1. The devices are then spray coated with a 110 micron thick layer of a water soluble mixture of polyvinylpyrrolidone and sorbitol mixed in a 1:25 weight ratio. This layer is then covered by a microporous wall 100 microns thick by spray coating a dichloromethane/methanol/water solution of a 1:1:1 blend of cellulose acetate having an acetyl content of 32%, cellulose acetate having an acetyl content of 39%, and sorbitol. The sorbitor is incorporated as a pore forming additive.

EXAMPLE 4

The procedures for preparing core tablets outlined in Example 3 are repeated with the exception that the C.R. NaSal particles are manufactured as a matrix rather than as coated particulates. The C.R. NaSal is prepared by granulating 500 g sodium salicylate mixed with 200 g lactose and 75 g cornstarch. The granulating fluid consists of Methocel K4M-Premium ® (hydroxypropylmethylcellulose) dissolved in a water:ethanol solvent blend. These granules are dried in a convection oven at 50° C. The resulting C.R. NaSal matrix particles release for an extended period which may be increased through increases in the weight percent ratio of Methocal K4M-Premium ® to sodium salicylate/lactose/cornstarch.

The cores are then coated with a microporous wall 100 microns thick by spraying a dichloromethane/methanol/water solution containing a 1:1:1 blend of cellulose acetate 32% acetyl, cellulose acetate 39% acetyl, and sorbitol. The sorbitol serves as a pore forming additive. A final semipermeable wall as described in Example 1 is then applied over the microporous wall and an 0.15 mm diameter hole drilled through the wall.

What is claimed is:

1. A drug delivery device for the controlled release of a therapeutically active ingredient into an environment of use which comprises:
   (A) a core composition comprising
      (a) a plurality of controlled release solubility modulating units consisting of solubility modulating agents each of which is either a surfactant or complexing agent, said surfactant being either (i) surrounded by a water insoluble microporous membrane containing at least one pore forming additive dispersed throughout said microporous membrane or (ii) dispersed in a matrix substrate and wherein said complexing agent is selected from the group consisting of: cyclodextrins, polyethylene glycols, polyvinylpyrridone, sodium, carboxymethylcellulose, salicylic acid, sodium salicylate, mandelic acid, sodium mandelate, caffeine, puric acid, quinhydrone, hydroquinone, tetracycline derivatives, 2-hydroxynicotinic acid, 3-hydroxy-3-phenyl propionic acid, phthalic acid, 3-4-dihydroxy cinnamic acid and the corresponding sodium salt; and,
      (b) a diffusible water soluble therapeutically active ingredient and
   (B) a water insoluble wall surrounding said core composition and prepared from a semi-permeable material substantially impermeable to core composition and permeable to the passage of an external fluid in the environment of use, with said wall having a means for release of the therapeutic agent through the water insoluble wall.

2. A drug-delivery device according to claim 1, wherein the solubility modulating agent is a surfactant selected from the group consisting of: sulfated, sulfonated or carboxylated esters, amides, alcohols, ethers, aromatic hydrocarbons, aliphatic hydrocarbons, acylated amino acids, and peptides; metal alkyl phosphates; primary, secondary, tertiary or quaternary alkylammonium salts, acylated polyamines and salts of heterocyclic amines; esters and ethers of polyoxyalkene amines, polyoxyalkene glycols, polyhydric alcohols or phenols.

3. A drug-delivery device according to claim 2, wherein the solubility modulating agent is a surfactant selected from the group consisting of: potassium laurate, sodium dodecyl sulfate, hexadecyl-sulphonic acid, sodium dioctylsulphosuccinate, hexa-decyl(cetyl)trimethylammonium bromide, dodecylpyridinium chloride, dodecylamine hydrochloride, N-dodecyl-N,N-dimethylbetaine, bile acids and salts, acacia, tragacanth, polyoxyethylated nonylphenols, sorbitan esters, poly-sorbates, polyoxyethylated t-octylphenols, polyoxyethylene lauryl ethers, polyoxyethylene cetyl ethers, polyoxy-ethylene stearyl ethers, polyoxyethylene oleyl ethers, polyoxyethylene stearates, poloxamer and poloxamine type polyoxyethylene-polyoxypropylene derivatives, phenothiazines and tricyclic antidepressants.

4. A drug-delivery device according to claim 1, wherein the solubility modulating agent is surrounded by a water insoluble microporous membrane containing at least one pore forming additive dispersed throughout said microporous membrane.

5. A drug delivery device according to claim 1, wherein the solubility modulating agent is dispersed in a matrix substrate.

6. A drug delivery device according to claim 4, wherein the matrix substrate are selected from hydroxypropyl cellulose, hydroxypropylmethyl cellulose, solid polyethylene glycols, carboxypolymethylene, silicone rubber, ethylene vinyl acetate, waxes, fats, fatty acids, fatty alcohols, triglycerides, poly(lactic acid), poly(ortho ester) and natural gums.

7. A drug delivery device according to claim 1, wherein the therapeutically active ingredient is soluble in an external fluid and exhibits an osmotic pressure gradient across the wall against the external fluid.

8. A drug delivery device according to claim 1, wherein the therapeutically active ingredient has limited solubility in the external fluid and is mixed with an osmotically effective solute that is soluble in the fluid, which exhibit an osmotic pressure gradient across the wall against the external fluid.

9. A drug delivery device according to claim 6, which further comprises in the core a member selected from water soluble excipients, buffers, insoluble buffers, bulking agents, and osmotic regulators.

10. A drug delivery device according to claim 1, wherein said water insoluble wall is 1 to 1,000 microns thick.

11. A drug delivery device according to claim 8 wherein said wall is 20 to 500 microns thick.

12. A drug delivery device according to claim 1, wherein at least 0.05 ng of active agent are used.

13. A drug-delivery device according to claim 10, wherein at least 1 microgram of active agent is used.

14. A drug delivery device according to claim 1, further comprising:

(C) 0 to 50 parts per 100 parts of (i) and (ii) of plasticizer and flux regulating additives and
(D) 0 to 40 parts per 100 parts of (i) and (ii), of surfactant additive.

15. A drug-delivery device according to claim 1, wherein said semipermeable material is a polymer selected from the group consisting of cellulose esters, cellulose ethers, acylated polysaccharides, polyurethane, polymers of acrylic and methacrylic acid and esters thereof, poly (ortho esters)s, polyacetals and mixtures thereof.

16. A drug-delivery device according to claim 1, further comprising a water insoluble, permeable, non-rate controlling microporous wall in direct contact with the water insoluble semipermeable wall.

17. A drug-delivery device according to claim 1, further comprising a microporous wall separated from the water insoluble semipermeable wall by a layer of fluid soluble material.

18. A drug delivery device according to claim 1, wherein the water insoluble wall comprises a lamina of adjacent semipermeable and microporous layers.

* * * * *

UNITED STATES PATENT AND TRADEMARK OFFICE
CERTIFICATE OF CORRECTION

PATENT NO. : 4,994,273

DATED : February 19, 1991

INVENTOR(S) : G.M. Zentner et al.

It is certified that error appears in the above-identified patent and that said Letters Patent is hereby corrected as shown below:

In Column 3, line 26, change "pre determined" to -- predetermined --.

In Column 4, line 48, change "compleses," to -- complexes, --.

In Column 4, line 49, change "compleses," to -- complexes, --.

In Column 4, line 54, change "cinnamic acid cyclodextrins" to
-- cinnamic acid, cyclodextrins --.

In Column 4, line 57, change "hydroquinone sodium" to
-- hydroquinone, sodium --.

In Column 4, line 57, change "aklyl" to -- alkyl --.

In Column 5, line 4, change "polyoxyalkene" to -- polyoxyalkylene --.

In Column 6, line 19, change "kinetics S" to -- kinetics, S --.

In Column 6, line 31, change "solubility desired" to
-- solubility, desired --.

In Column 7, line 49, change "avernectubsm" to -- avermectins --.

In Column 7, line 49, change "dexanethasone," to -- dexamethasone, --.

In Column 7, line 51, change "norlfoxacin" to -- norfloxacin --.

In Column 7, line 66, change "gms" to -- g --.

In Column 7, line 68, change "1.5 mg" to -- 1.5 g --.

In Column 8, line 64, change "triaceylates" to -- triacylates --.

In Column 12, line 13, change "dichloridemethanol" to
-- dichloride-methanol --.

In Column 15, line 25, change "qlucose" to -- glucose --.

UNITED STATES PATENT AND TRADEMARK OFFICE
CERTIFICATE OF CORRECTION

PATENT NO. : 4,994,273

DATED : February 19, 1991

INVENTOR(S) : G.M. Zentner et al.

It is certified that error appears in the above-identified patent and that said Letters Patent is hereby corrected as shown below:

In Column 15, line 63, change "polyvinyl-pyrrolidone" to
-- polyvinyl pyrrolidone --.

In Column 16, line 4, change "based" to -- blend --.

In Column 16, line 9, change "January" to -- Jenway --.

In Column 16, line 38, change "particules." to -- particles. -- .

In Column 17, line 1, change "polyvinylpyrrolidione" to
-- polyvinyl pyrrolidone -- .

In Column 17, line 35, change "sorbitor" to -- sorbitol --.

At Claim 1(A)(a)(ii), in Column 18, line 7 - 8, change "sodium, carboxymethylcellulose," to -- sodium carboxymethylcellulose, -- .

At Claim 1(A)(a)(ii), in Column 18, line 10, change "puric acid" to
-- picric acid --.

At Claim 1(A)(a)(ii), in Column 18, line 14, change "salt;" to -- salts' --.

At Claim 2, in Column 18, line 33 and 34, change "polyoxyalkene" to
-- polyoxyalkylene --.

UNITED STATES PATENT AND TRADEMARK OFFICE
CERTIFICATE OF CORRECTION

PATENT NO. : 4,994,273

DATED : February 19, 1991

INVENTOR(S) : G. M. Zentner et al

It is certified that error appears in the above-identified patent and that said Letters Patent is hereby corrected as shown below:

At Claim 2, in Column 18, line 33 and 34, change "polyoxyalkene" to --polyoxyalkylene--.

Signed and Sealed this

Third Day of March, 1992

Attest:

HARRY F. MANBECK, JR.

*Attesting Officer*  *Commissioner of Patents and Trademarks*